US006443366B1

(12) United States Patent
Hirota et al.

(10) Patent No.: US 6,443,366 B1
(45) Date of Patent: Sep. 3, 2002

(54) LIQUID-DROP DISCHARGE DEVICE

(75) Inventors: Toshikazu Hirota, Owariasahi; Takao Ohnishi; Yukihisa Takeuchi, both of Aichi-ken, all of (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 09/685,492

(22) Filed: Oct. 10, 2000

(30) Foreign Application Priority Data

Oct. 15, 1999 (JP) .......................................... 11-294412

(51) Int. Cl.[7] ............................ B05B 1/08; B05B 3/04; A61M 11/02

(52) U.S. Cl. ............................... 239/102.2; 239/102.1; 239/338

(58) Field of Search .......................... 239/102.1, 102.2, 239/337, 373, 338, 533.6, 533.1, 533.2, 58; 222/240; 347/47, 68; 310/317, 316.01, 324; 118/320, 314, 56

(56) References Cited

U.S. PATENT DOCUMENTS 4,294,407 A * 10/1981 Reichl et al. ............ 239/102.2
4,301,093 A * 11/1981 Eck ......................... 239/102.2
5,361,989 A * 11/1994 Merchat et al. .......... 239/102.2
5,518,179 A * 5/1996 Humberstone et al. .. 239/102.2
5,534,069 A * 7/1996 Kuwabara et al. .......... 118/719
5,586,550 A * 12/1996 Ivri et al. .............. 128/200.16
5,758,637 A * 6/1998 Ivri et al. .............. 128/200.16
5,976,259 A * 11/1999 Yamazaki
6,102,298 A * 8/2000 Bush et al. .................... 239/4

* cited by examiner

*Primary Examiner*—Lesley D. Morris
*Assistant Examiner*—Davis Hwu
(74) *Attorney, Agent, or Firm*—Burr & Brown

(57) ABSTRACT

A liquid-drop discharge device is provided including a float cell provided with a valve and communicating to a liquid storage tank, a liquid discharge mechanism for discharging liquid within the float cell, and a reaction cell provided with a space into which fluid is discharged from the liquid discharge mechanism for collecting the discharged fluid. Air is supplied to the reaction cell for collecting liquid or minute particles, and an internal pressure P1 of the liquid storage tank or the float cell and an internal pressure P3 of the reaction cell are set such that a relationship of P1=P3, in which the pressures are identical to atmospheric pressure, or P1>P3, to supply stronger air, is satisfied.

12 Claims, 9 Drawing Sheets

LIQUID-DROP DISCHARGE DEVICE

BACKGROUND OF THE INVENTION

1. Field of the Invention

The present invention relates to a liquid-drop discharge device used in various machineries for processing liquid by performing discharge of liquid.

2. Description of the Prior Art

Ink jet discharge devices as disclosed, for instance, in Japanese Patent Unexamined Publication No. 6-40030 (1994) are conventionally known types of devices for discharging liquid in form of minute particles used in particular fields. However, such discharge devices are used in offices or schools under relatively stationary conditions with little fluctuations in temperature or pressure of peripheral environments when being used, and are not exposed to significant fluctuations in operating environments.

On the other hand, minute powders of various chemicals are being used as auxiliary products for manufacturing semiconductors or the like, wherein the required standards in view of particle size can not be achieved by simply using mechanical crushing means, and developments in manufacturing methods of new types of powder are desired. It is urgently necessary to employ, as one exemplary method, a method for supplying raw materials in forms of minute particles to reaction cells such as drying chambers in a stable manner. Thus, devices that may be used with such methods for dropping liquid as particles from several hundredths of a nanometer to several tenths of a micron in a stable and controlled manner are needed.

While remarkable fluctuations in environments of discharge spaces are likely to occur at the time of operating such devices, due to fluctuations in operating conditions or the like, it is presently the case that no device has yet been proposed with which liquid can be supplied as minute particles in a desirable manner even though in the presence of fluctuations in discharge spaces.

SUMMARY OF THE INVENTION

The present invention has been made to provide a liquid discharge device for raw materials, or the like, of an arrangement that is capable of continuously adjusting conditions for discharging liquid to be an optimal condition in accordance with fluctuating peripheral environments, even when an environment of discharge space radically and abruptly fluctuates, or air bubbles are present. Further, a liquid discharge device that is capable of steadily discharging liquid regardless of the size of the operating range is desired.

For solving the above objects, the inventors of the present invention have devised an invention that is related to a liquid-drop discharge device comprising a liquid storage tank, a liquid discharge means for discharging liquid within the liquid storage tank, and a reaction cell provided with a space into which liquid is discharged from the liquid discharge means. The liquid discharge means comprises a discharge outlet provided at an end portion of a flow path opening to the reaction cell, an opening degree means for adjusting an opening degree of the discharge outlet, and an oscillating means for applying oscillation to liquid introduced into the flow path. Accordingly, a flow of liquid that has been oscillated by the oscillating means is sucked and atomized from an air-contacting surface of the discharge outlet by an internal pressure of the reaction cell when $P1 \geqq P3$, which is satisfied when the internal pressure of the liquid storage tank and the internal pressure of the reaction cell are respectively defined as P1 and P3.

With this arrangement, liquid may be discharged in a steady and well-controlled manner despite the presence of air bubbles in liquid within the flow path, wherein the flow of liquid applied with minute oscillation by the oscillating means is atomized, and atomization caused through suction of the air-contacting surface of the discharge outlet by the internal pressure of the reaction cell may be continued while maintaining a minute spraying condition. When the internal pressure of the liquid storage tank and the internal pressure of the reaction cell are identical, spraying of a small amount may be performed even through fibrillation of the oscillating means, so that it is possible to cope with various amounts of spraying of a wide range from a large capacity to a small amount.

It should be noted that as an exemplary means for setting the internal pressure P3 of the reaction cell to be not more than the internal pressure P1 of the liquid storage tank, air is supplied to the reaction cell, and if necessary, a negative pressure may be effectively achieved by narrowing a sectional surface area of a portion of the reaction cell that is open to the discharge outlet in contrast to other portions.

The present invention further relates to a liquid-drop discharge device wherein the liquid discharge means comprises a discharge outlet provided at an end of a flow path opening to the reaction cell, and an oscillating means concurrently provided with a function of adjusting an opening degree of the discharge outlet and of applying fibrillation to liquid introduced into the flow path through the discharge outlet. With this arrangement, it is possible to simplify arrangements of driving portions and to decrease manufacturing costs for performing atomization in an effective manner.

It should be noted that the concurrently used oscillating means may be arranged by employing a method in which instructions for adjusting opening degrees are issued at the time of starting operation, instructions for applying minute oscillation are repetitively issued in a single structure, or a method in which a structure for adjusting the opening degree and a structure for applying minute oscillation are laminated and provided at an end of the flow path.

The opening degree means may be arranged in a valve arrangement, in which a valve body provided at a thin film portion of a wall portion of a flow path end portion is arranged adjacent to a seat opening to the reaction cell for varying an inner diameter of the flow path, wherein a projecting member formed inside of the flow path for narrowing the inner diameter of the flow path may be provided either at the valve seat or the valve body. A pressurizing member provided outside of the thin film portion of the wall portion of the flow path end portion may be comprised by a laminated actuator, a thin film actuator with a comb-like electrode arrangement of a style in which piezoelectric bodies are arranged between cathode and anode comb-teeth or in which the piezoelectric bodies are arranged to be parallel with respect to the cathode and anode comb-like arrangement, or a solenoid coil.

It is particularly preferable that the liquid discharge means be comprised of a flow path having a wall surface with at least one surface thereof being arranged to be thinner than the remaining surfaces. It is also preferable that the opening degree means be arranged in that the sectional surface area of the flow path is varied by utilizing distortion of a piezoelectric/electrostrictive element provided at least at one portion of the thin wall portion of the flow path end portion.

With this arrangement, it is possible to perform discharge at low electric consumption and in a well-controlled manner, and to further decrease manufacturing costs. When the opening degree means is concurrently provided as the oscillating means, it is favorably possible to perform high-frequency oscillation and to perform rapid adjustment of the opening degree. In order to enable large displacements of the thin film portion of the wall portion of the flow path for adjusting the opening degree, it is possible to form the end portion of the flow path to be wide in a direction orthogonal to a direction of displacement and to provide the discharge outlet in a center thereof as the end portion of the flow path.

The oscillating means may be comprised of a laminated actuator or a thin film actuator, which is arranged to pinch piezoelectric bodies between cathodes and anodes, outside of the thin film portion of the wall portion of the flow path. It is particularly preferable that the liquid discharge means be comprised of a flow path having a wall surface with at least one surface thereof being arranged to be thinner than remaining surfaces, and that the oscillating means be arranged to apply minute oscillation to liquid by utilizing distortion of a piezoelectric/electrostrictive element provided at least at one portion of the thin wall portion of the flow path. With this arrangement, it is not only possible to provide an oscillating means of large amplitude at low costs, but also to perform high-frequency driving at low voltage.

The oscillating means provided outside of the thin film portion of the wall portion may be disposed to surround the discharge outlet in which a piercing hole for the opening degree means is provided at a center thereof to extend along an outer periphery of the discharge outlet, or a rectangular oscillating member may be disposed proximate to the discharge outlet. Either one or a plurality of rectangular oscillating members may be provided at this time, and when a plurality thereof are provided, they may be disposed around the discharge outlet in a radial manner. For transmitting oscillation to liquid in an effective manner, the oscillating means may be formed at more upper thin wall portions when compared to the opening degree means, and oscillating members located remote from the discharge outlet may be disposed to be oblique with respect to the wall surface, for making directions of amplitude face the discharge outlet such that oscillation may be focused at the discharge outlet.

It is preferable that the discharge outlet be arranged in that its portion opening to the reaction cell is formed to assume a shape of an elongated hole for increasing a surface area of discharge and an amount of spraying. It is also preferable to dispose a float cell that is connected to between the liquid storage tank and the liquid discharge means with a check valve being formed at the liquid storage tank for functioning to maintain a constant liquid surface with a constant capacity. The back pressure of the liquid from the liquid storage tank may thus be made constant and leakage of liquid from the discharge outlet upon being pressurized may be prevented.

DESCRIPTION OF THE PREFERRED EMBODIMENTS

Forms for embodying the liquid-drop discharge device according to the present invention will now be explained in detail.

Figure 1:
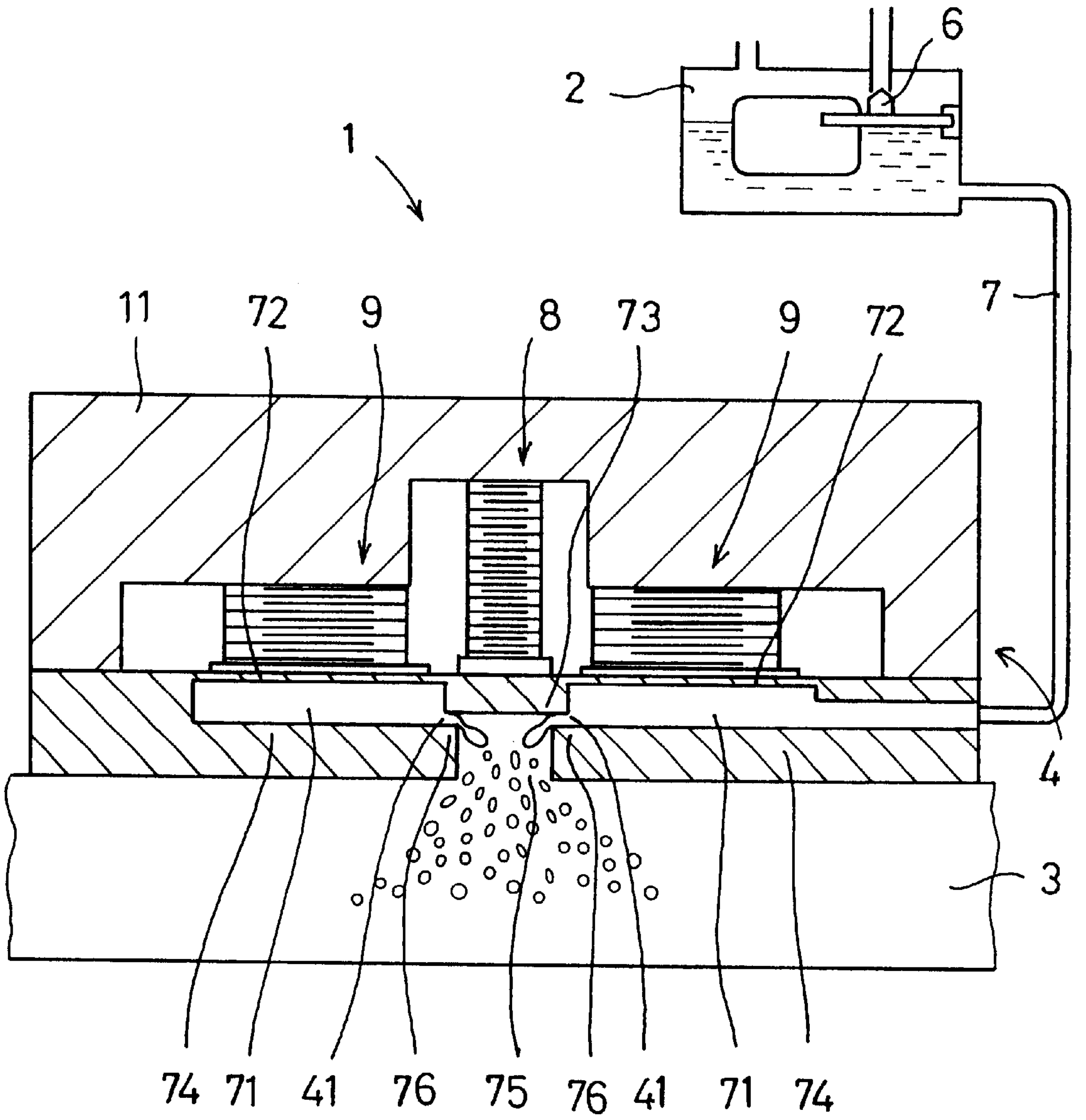
FIG. 1 is an end elevation view in which a liquid-drop discharge device is longitudinally cut along its center.
Figure 2:
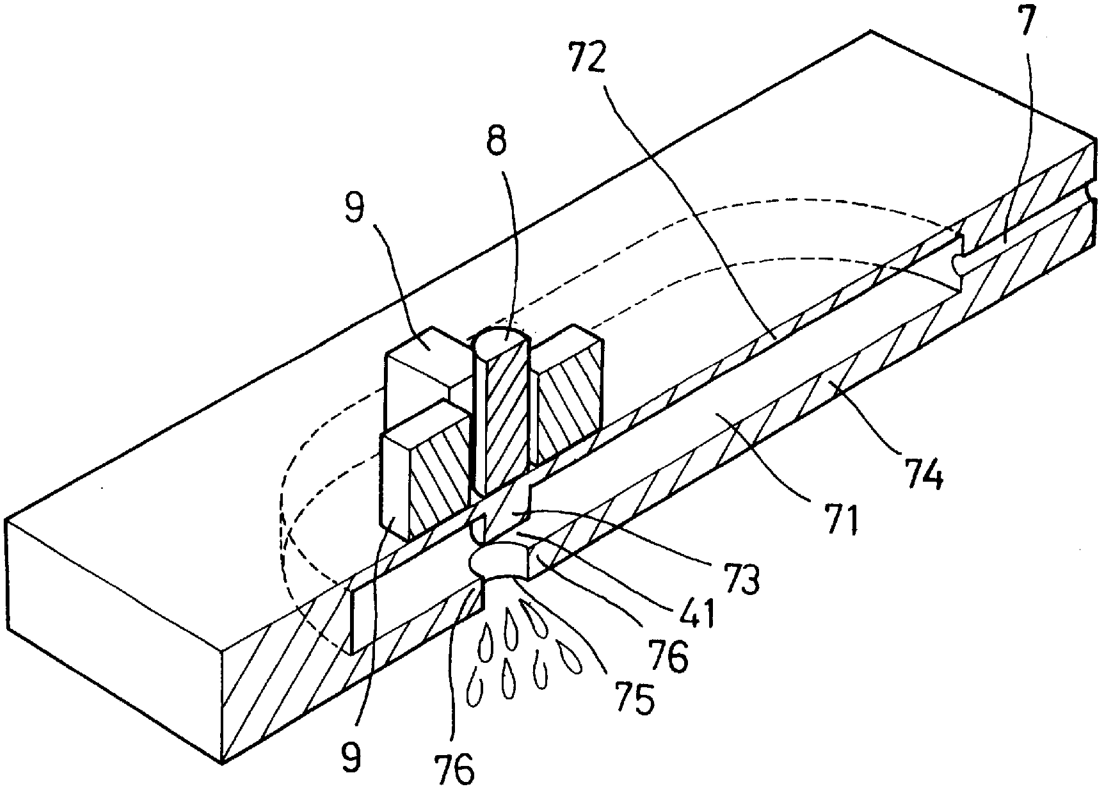
FIG. 2 is an explanatory view showing FIG. 1 in a diagonal manner.

FIG. 1 is an end elevation view in which the liquid-drop discharge device is longitudinally cut along its center, and FIG. 2 is an explanatory view showing FIG. 1 in a diagonal manner.

The liquid-drop discharge device 1 is comprised of a float cell 2 provided with a valve 6 and communicating to a liquid storage tank, a liquid discharge means 4 for discharging liquid within the float cell 2, and a reaction cell 3 provided with a space into which fluid is discharged from the liquid discharge means 4 for collecting the discharged fluid. Air is being supplied to the reaction cell 3 for collecting liquid or minute particles, and an internal pressure P1 of the liquid storage tank or the float cell 2 and an internal pressure P3 of the reaction cell 3 are set such that a relationship of P1=P3, in which the pressures are identical to atmospheric pressure, or P1>P3 to supply stronger air, is satisfied.

Since the liquid discharge means 4 is provided with a discharge outlet 41 provided at an end of a flow path 7 opening to the reaction cell 3, an opening degree means 8 for adjusting an opening degree of the discharge outlet 41, and an oscillating means 9 for applying oscillation to liquid introduced into the flow path 7, a flow of liquid oscillated by the oscillating means 9 is sucked and atomized from an air-contacting surface of the discharge outlet 41 by the internal pressure of the reaction cell 3.

An oscillating chamber 71 provided with a wide space is formed at the end of the flow path 7 with an upper wall 72 being formed to be like a thin plate. By providing a valve body 73 projecting in a downward direction from a part of the upper wall, an aperture portion 75 opening to the reaction cell 3 that pierces through a lower wall 74 opposing the valve body 73, and a valve seat 76 at a peripheral edge of the aperture 75 that comes into contact with the valve body 73 when it is descent to a lowermost position, a clearance formed between the valve body 73 and the valve seat 76 comprises the discharge outlet 41.

A lower end portion of the opening degree means 8 for pressing the upper wall 72 downward in vertical directions abuts from an upper direction of the valve body 73 with the upper wall 72 being interposed between, and upper end of the opening degree means 8 is fixed to a base frame 11 covering an upper region of the oscillating chamber 71. The opening degree means 8 is comprised of a laminated actuator in which a plurality of piezoelectric films pinched between cathode and anode electrodes are laminated. Oscillating means 9, which is respectively comprised of a laminated actuator, the lower end of which similarly contacts the upper wall 72 and which upper end is fixed to the base frame 11, is provided in a periphery of the opening degree means 8. Since an amount of amplitude of oscillation of the oscillating means 9 may be smaller than that of the opening degree means 8, the number of lamination for the laminated actuator may also be smaller.

It should be noted that the illustrated laminated actuator is of a type utilizing piezoelectric longitudinal effects in which distortion in an extending direction of the piezoelectric bodies are utilized. It is alternatively possible that it be of a type utilizing piezoelectric transverse effects in which distortion in a shrinking direction of the piezoelectric bodies are utilized.

For performing discharge of liquid-drops, an amount of discharge is first adjusted by adjusting the piezoelectric/electrostrictive element 83 of the opening degree means 8 in accordance with a desired amount of discharge of liquid-drops by varying a size of the clearance of the discharge outlet 41. By applying oscillation to the upper wall 72 of the oscillating chamber 71 through conducting electric power to the piezoelectric/electrostrictive element 93 of the oscillating means 9, the flow of liquid filling the oscillating chamber 71 is sucked and atomized from the air-contacting surface of the discharge outlet 41 by the negative pressure of the reaction cell 3.

It should be noted that signals impressed/conducted to the opening degree means 8 are output in accordance with required amounts of discharge of liquid-drops, while the signals impressed/conducted to the oscillating means 9 are signals of high-frequency regions of not less than several tens of kHz. If required by the oscillating means 9, the signals may be modulated to a low frequency of several tenths of a Hz.

Figure 3:
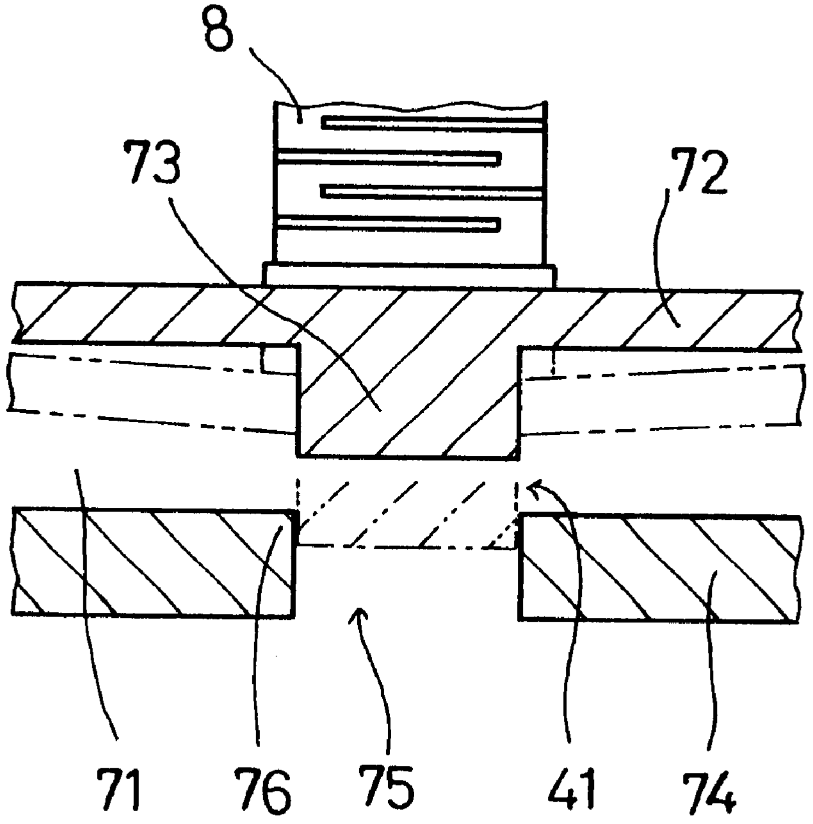
FIG. 3 is an explanatory view showing another form of embodiment of an opening degree means.

FIG. 3 and other drawings illustrate another embodiment. FIG. 3 illustrates another form of embodiment of the valve body 73 of the opening degree means 8. In this case, the shape of the valve body 73 is made identical to the end edge of the aperture portion 75, so that shielding properties of the discharge outlet 41 may be improved when the valve body 73 is descent to its lowermost position and the tip end of the valve body 73 is inserted into the aperture 75.

Figure 4:
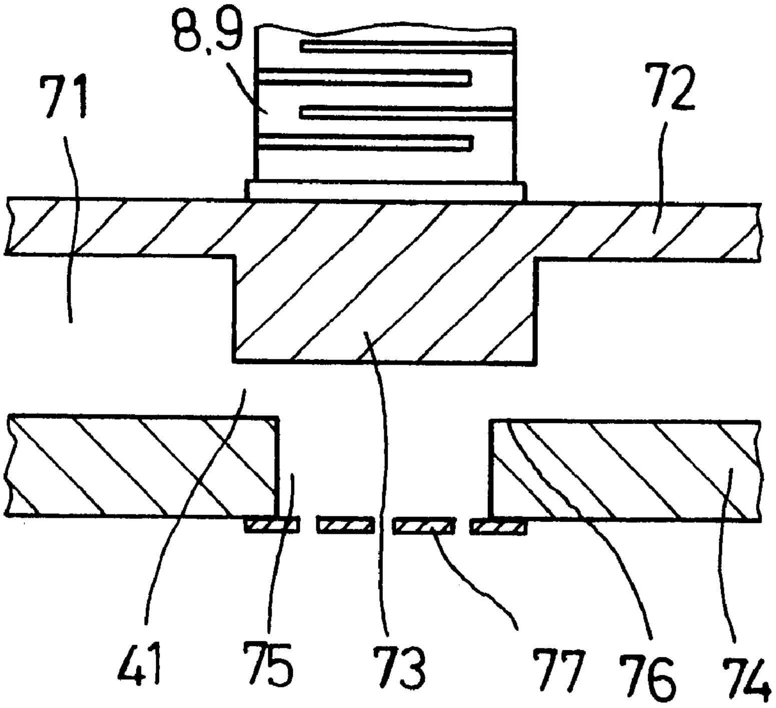
FIG. 4 is an explanatory view showing a form of embodiment in which a thin plate is mounted to an aperture portion.

In FIG. 4, a thin plate 77 formed with a plurality of minute pores is provided outside the aperture portion 75. With this arrangement, it is possible to prevent degradations in atomizing performance in case liquid-drops with inferior atomizing properties shall be output from the discharge outlet 41 at the time the internal pressure P3 of the reaction cell 3 is abruptly varied, or during a transition period immediately after impressing a signal. The thin plate 77 formed with a plurality of minute pores may alternatively be a mesh plate with an aperture rate suitable of the purpose or fluidity.

Figure 5:
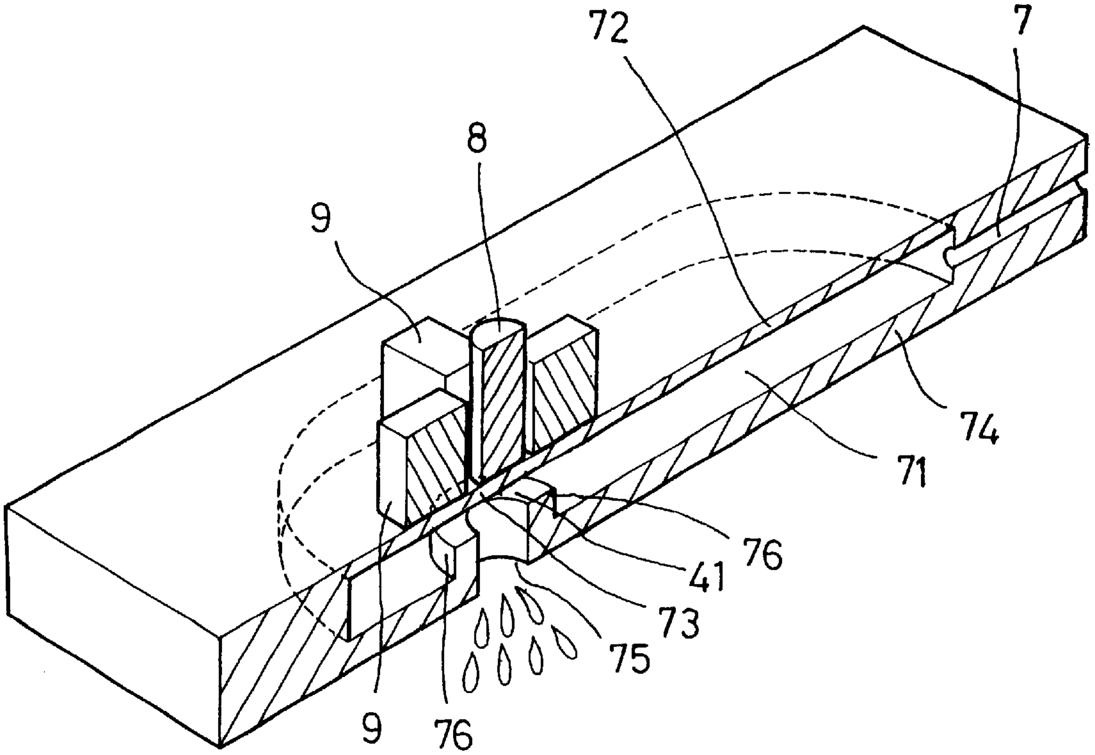
FIG. 5 is an explanatory view showing another form of embodiment.

FIG. 5 and other drawings illustrate another form of embodiment corresponding to FIG. 2. While the discharge outlet 41 as illustrated in FIG. 1 is arranged in that the valve body 73 is provided to project from the upper wall 72 and the valve body 73 is pressed downward by the opening degree means 8, that of the FIG. 5 is arranged in that the valve body 76 is formed to project in an upward direction of a peripheral edge of the aperture portion 75 for pressing the valve body 73 (which has a common plane with the upper wall 72), downward by means of the opening degree means 8.

Figure 6:
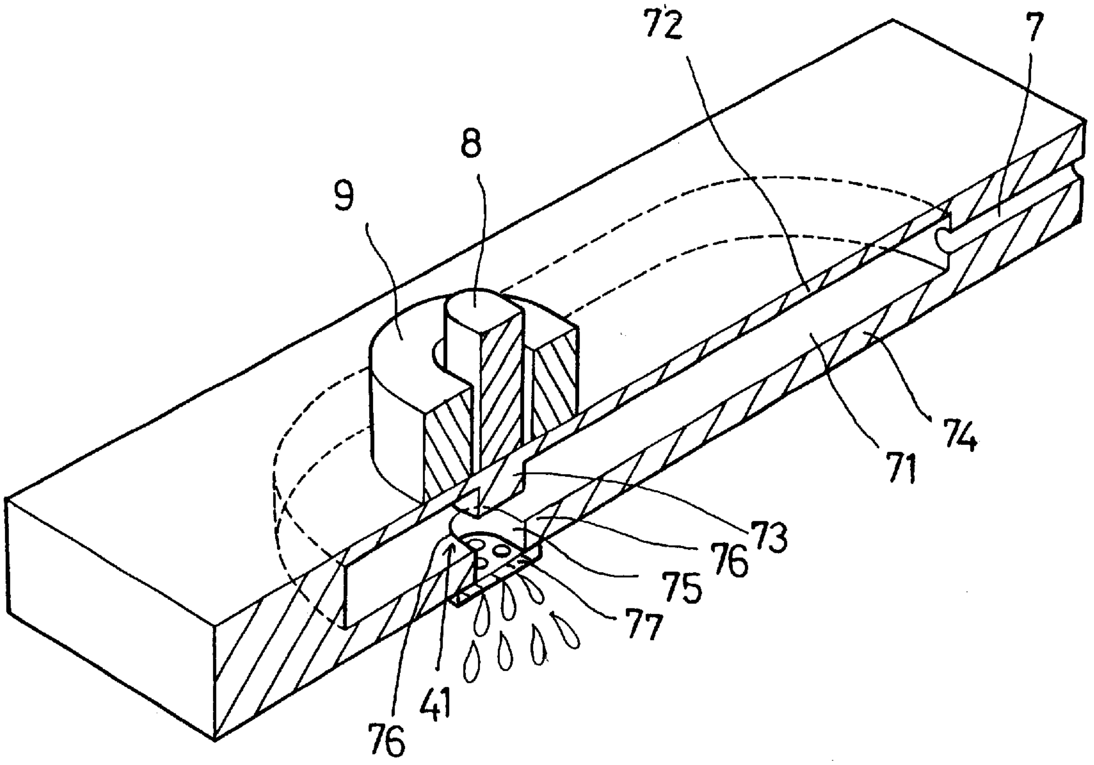
FIG. 6 is an explanatory view showing another form of embodiment.

While the oscillating means 9 as illustrated in FIGS. 1 and 2 are disposed in that a plurality of laminated bodies formed to assume box-like shapes are disposed in a radial manner around the opening degree means 8, that of FIG. 6 is a tubular-shaped oscillating means 9 surrounding a columnar opening degree means 8. The shape of the aperture portion 75 of the discharge outlet 41 is formed to assume a shape of an elongated hole extending in a width direction of the oscillating chamber 71, and a thin plate 77 provided with a plurality of minute pores is mounted to outside of the aperture portion 75.

Figure 7:
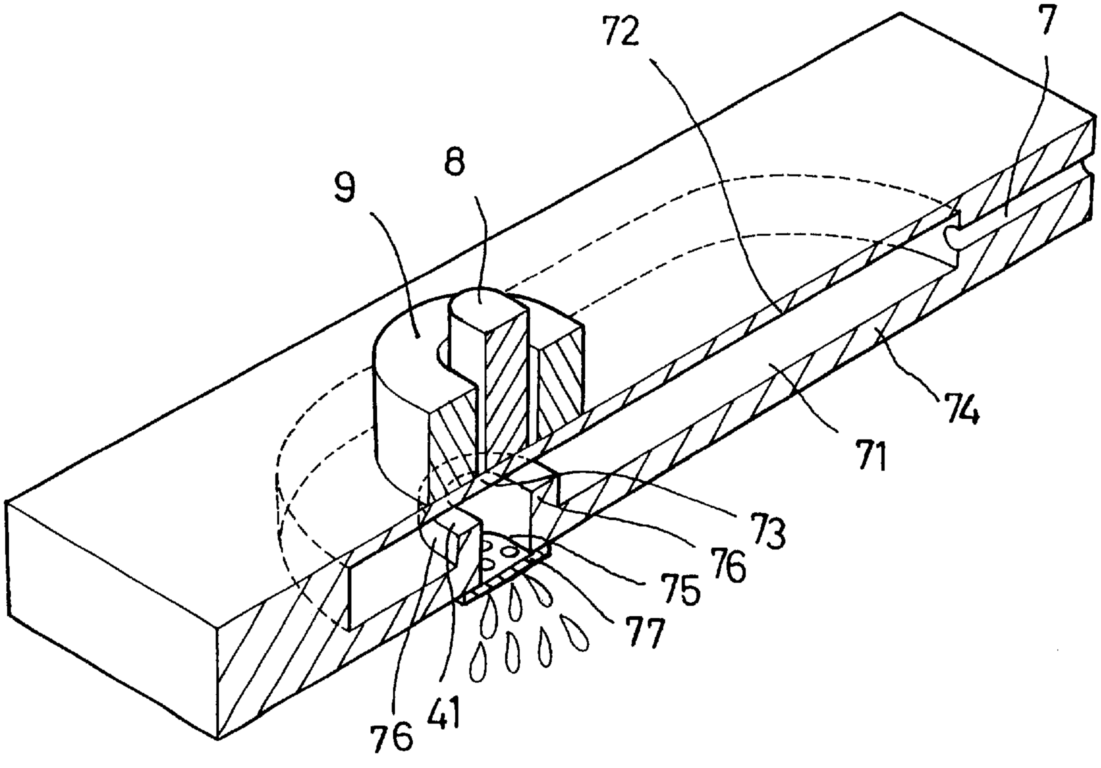
FIG. 7 is an explanatory view showing another form of embodiment.

FIG. 7 illustrates an arrangement in which the discharge outlet 41 of FIG. 5, and the oscillating means 9, aperture portion 75 and the thin plate 77 of FIG. 6 are concurrently used. It should be noted that sizes of the minute pores are illustrated to be larger in contrast to the aperture portion 75.

Figure 8:
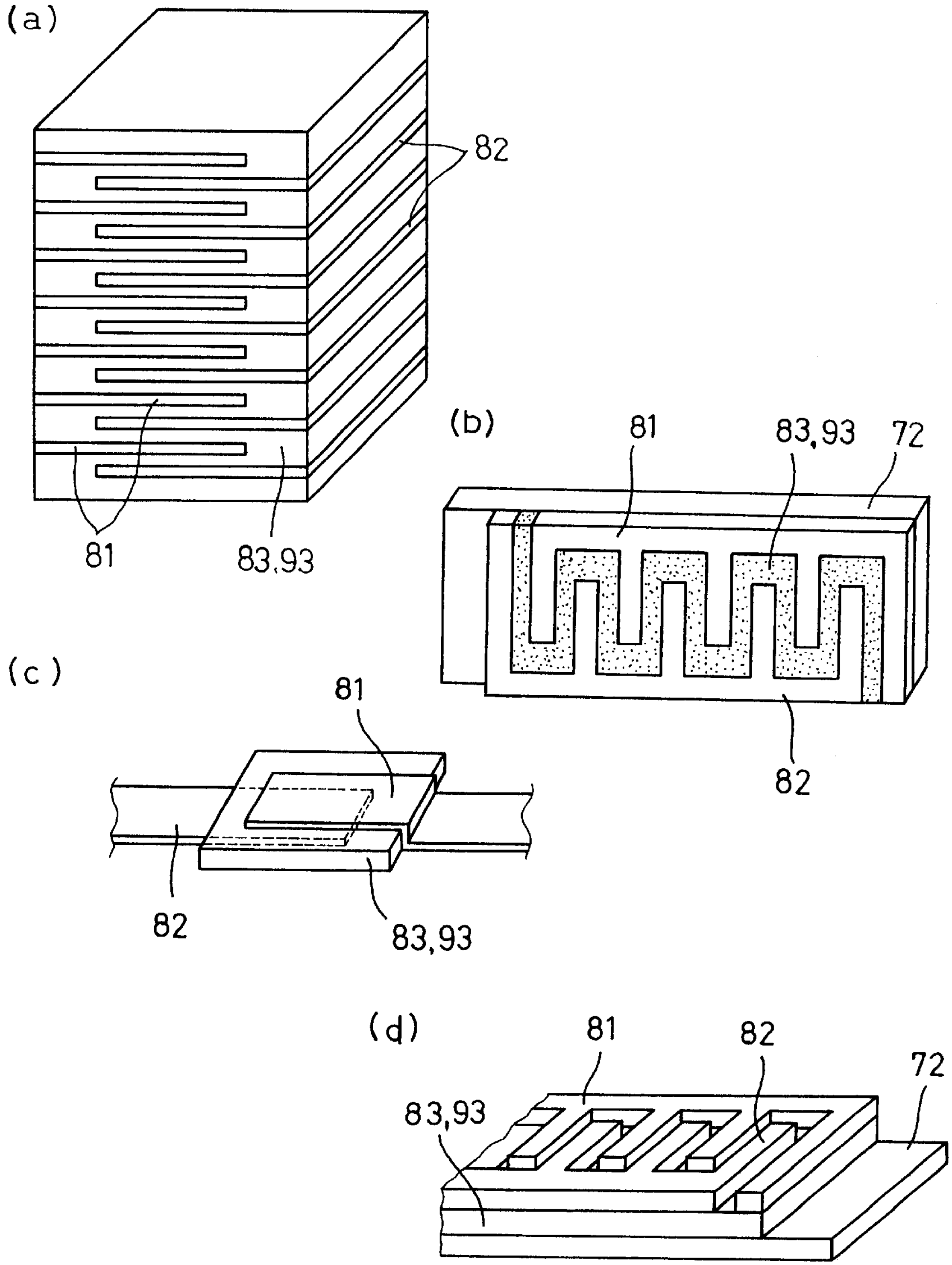
FIG. 8 is an explanatory view showing another form of embodiment of an actuator.

FIG. 8 illustrates another form of embodiment of the aperture degree means 8 and the oscillating means 9, wherein the aperture degree means 8 and the oscillating means 9 of FIG. 1 may be comprised, as illustrated in FIG. 8(*a*), of a laminated actuator in which a plurality of piezoelectric/electrostrictive films 83, 93 pinched between cathode and anode electrodes 81, 82 are laminated. It is alternatively possible to fill piezoelectric/electrostrictive films 83, 93 between clearances in which comb-teeth of comb-like electrode plates are mutually meshed with each other as illustrated in FIG. 8(*b*), to pinch the piezoelectric/electrostrictive films between plate-like cathodes and anodes as illustrated in FIG. 8(*c*), or to make comb-teeth of comb-like electrode plates meshed with each other with a clearance being maintained between in which piezoelectric/electrostrictive films 83, 93 are pinched at lower portions of the electrode plates as illustrated in FIG. 8(*d*).

Figure 9:
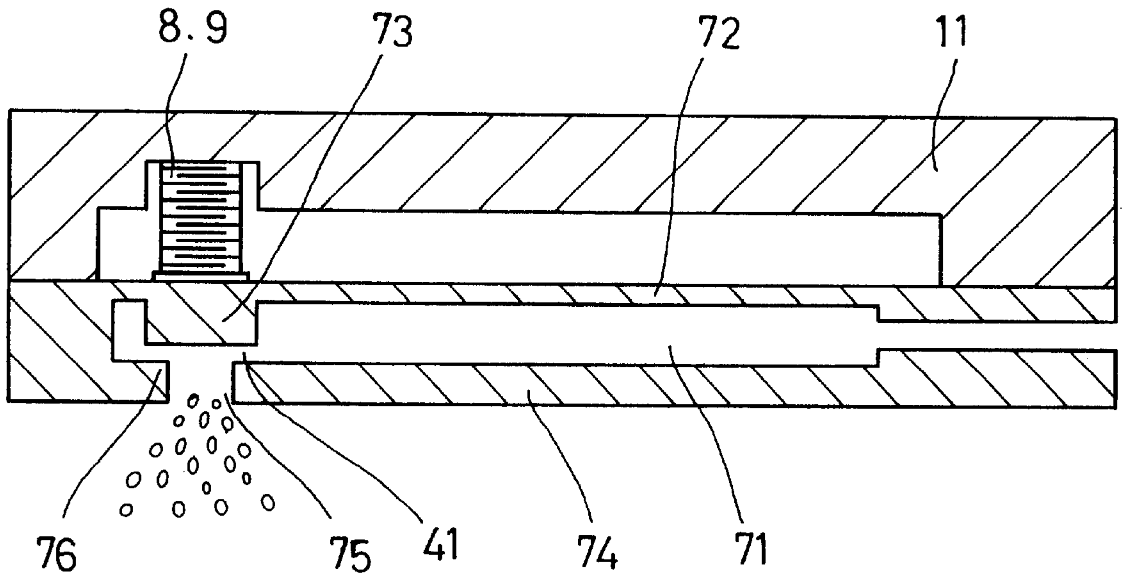
FIG. 9 is an explanatory view showing a form of embodiment in which the opening degree means and an oscillating means are concurrently used.

FIG. 9 illustrates a form of embodiment in which a single laminated actuator concurrently serves as the aperture degree means 8 and the oscillating means 9. By adjusting the opening degree and applying oscillation by a single actuator like in this case, impressing/conducting signals for oscillation are repetitively sent with impressing/conducting signals corresponding to instructions for adjusting the opening degree.

It should be noted that shapes, sizes or materials of the respective members shall be determined in view of purpose of use or physical and chemical characteristics of liquid to be discharged. The reaction cell 3, for instance, may be made of stainless steel, of a member having an inner surface lined by glass or similar materials when the cell shall act as a reaction unit for gaseous reaction, or made of stainless steel members when the cell shall act as a drying chamber for liquid. The member comprising the oscillating chamber 71 is preferably one laminated and integrally baked with a ceramic material in view of chemical resistance and solvent resistance. It may also be of metallic material in view of durability to oscillation, when metal is laminated and formed through adhesion using an adhesive, brazing or using a metal diffusion method.

As explained so far, according to the present invention, the liquid discharge means is comprised with a discharge outlet provided at an end portion of a flow path opening to the reaction cell, an opening degree means for adjusting an opening degree of the discharge outlet, and an oscillating means for applying oscillation to liquid introduced into the flow path, wherein a flow of liquid that has been oscillated by the oscillating means is sucked and atomized from an air-contacting surface of the discharge outlet by an internal pressure of the reaction cell. With this arrangement, liquid may be discharged in a steady and well-controlled manner despite the presence of air bubbles in liquid within the flow path.

The flow of liquid applied with minute oscillation by the oscillating means is atomized, and atomization caused through suction of the air-contacting surface of the discharge outlet by the internal pressure of the reaction cell may be continued while maintaining a minute spraying condition. When the internal pressure of the liquid storage tank and the internal pressure of the reaction cell are identical, spraying of a small amount may be performed even through fibrillation of the oscillating means, so that it is possible to cope with various amounts of spraying of a wide range from a large capacity to a small amount.

What is claimed is:

1. A liquid-drop discharge device comprising a liquid storage tank, a liquid discharge means for discharging liquid supplied from the liquid storage tank, and a reaction cell provided with a space into which liquid is discharged from the liquid discharge means, the liquid discharge means comprising a discharge outlet provided at an end portion of a flow path opening to the reaction cell, an opening degree means for adjusting an opening degree of the discharge outlet, and an oscillating means for applying oscillation to liquid introduced into the flow path, wherein a flow of liquid that has been oscillated by the oscillating means is sucked and atomized from an air-contracting surface of the discharge outlet by an internal pressure of the reaction cell when P1≧P3 is satisfied, P1 being an internal pressure of the liquid storage tank and P3 being an internal pressure of the reaction cell.

2. The liquid-drop discharge device as claimed in claim 1, wherein that portion of the discharge outlet that is open to the reaction cell is in the shape of an elongated hole.

3. The liquid-drop discharge device as claimed in claim 1, further comprising a float cell connected between the liquid storage tank and the liquid discharge means, said float cell comprising a check valve in communication with the liquid storage tank to maintain a constant amount of liquid in the float cell.

4. A liquid-drop discharge device comprising a liquid storage tank, a liquid discharge means for discharging liquid supplied from the liquid storage tank, and a reaction cell provided with a space into which liquid is discharged from the liquid discharge means, the liquid discharge means comprising a discharge outlet provided at an end portion of a flow path opening to the reaction cell, and an oscillating means for adjusting an opening degree of the discharge outlet and for applying oscillation to liquid introduced into the flow path, wherein a flow of liquid that has been oscillated by the oscillating means is sucked and atomized from an air-contacting surface of the discharge outlet by an internal pressure of the reaction cell while the amount of liquid sprayed from the discharge outlet is adjusted by said oscillating means when P1≧P3, P1 being an internal pressure of the liquid storage tank and P3 being the internal pressure of the reaction cell.

5. The liquid-drop discharge device as claimed in claim 4, wherein that portion of the discharge outlet that is open to the reaction cell is in the shape of an elongated hole.

6. The liquid-drop discharge device as claimed in claim 4, further comprising a float cell connected between the liquid storage tank and the liquid discharge means, said float cell comprising a check valve in communication with the liquid storage tank to maintain a constant amount of liquid in the float cell.

7. A liquid-drop discharge device comprising a liquid storage tank, a liquid discharge means for discharging liquid supplied from the liquid storage tank, and a reaction cell provided with a space into which liquid is discharged from the liquid discharge means, the liquid discharge means comprising a discharge outlet provided at an end portion of a flow path opening to the reaction cell, and an oscillating means for adjusting an opening degree of the discharge outlet and for applying oscillation to liquid introduced into the flow path, wherein a flow of liquid that has been oscillated by said oscillating means is sucked and atomized from an air-contacting surface of the discharge outlet by an internal pressure of the reaction cell while the amount of liquid sprayed from the discharge outlet is adjusted by said oscillating means when P1≧P3, P1 being an internal pressure of the liquid storage tank and P3 being the internal pressure of the reaction cell;

wherein the flow path has at least one section that is thinner than the remaining section thereof, and wherein said oscillating means is arranged to apply minute oscillation to liquid in the flow path by utilizing distortion of a piezoelectric/electrostrictive element provided at least at one portion of said at least one section of the flow path.

8. A liquid-drop discharge device comprising a liquid storage tank, a liquid discharge means for discharging liquid supplied from the liquid storage tank, and a reaction cell provided with a space into which liquid is discharged from the liquid discharge means, the liquid discharge means comprising a discharge outlet provided at an end portion of a flow path having at least one section that is thinner than the remaining section thereof and opening to the reaction cell, an opening degree means for adjusting an opening degree of the discharge outlet being arranged such that the cross-sectional area of the flow path is varied by utilizing distortion of a piezoelectric/electrostrictive element provided at least at one portion of said at least one section of the flow path, and an oscillating means for applying oscillation to liquid introduced into the flow path, wherein a flow of liquid that has been oscillated by the oscillating means is sucked and atomized from an air-contracting surface of the discharge outlet by an internal pressure of the reaction cell when P1≧P3 is satisfied, P1 being an internal pressure of the liquid storage tank and P3 being an internal pressure of the reaction cell.

9. The liquid-drop discharge device as claimed in claim 8, wherein said liquid discharge means father comprises a flow path having a wall surface with at least one surface thereof being arranged to be thinner than remaining surfaces, and wherein the oscillating means is arranged to apply minute oscillation to liquid by utilizing distortion of a piezoelectric/electrostrictive element provided at least at one portion of the thin wall portion of the flow pat.

10. The liquid-drop discharge device as claimed in claim 8, wherein that portion of the discharge outlet that is open to the reaction cell is in the shape of an elongated hole.

11. The liquid-drop discharge device as claimed in claim 8, further comprising a float cell connected between the liquid storage tank and the liquid discharge means, said float cell comprising a check valve in communication with the liquid storage tank to maintain a constant amount of liquid in the float cell.

12. A liquid-drop discharge device comprising a liquid storage tank, a liquid discharge means for discharging liquid supplied from the liquid storage tank, and a reaction cell provided with a space into which liquid is discharged from the liquid discharge means, the liquid discharge means comprising a discharge outlet provided at an end portion of a flow path having at least one section that is thinner than the remaining section thereof and opening to the reaction cell, an opening degree means for adjusting an opening degree of the discharge outlet, and an oscillating means arranged to apply minute oscillation to liquid in the flow path by utilizing distortion of a piezoelectric/electrostrictive element provided at least at one portion of said at least one section of the flow path, wherein a flow of liquid that has been oscillated by the oscillating means is sucked and atomized from an air-contracting surface of the discharge outlet by an internal pressure of the reaction cell when P1≧P3 is satisfied, P1 being an internal pressure of the liquid storage tank and P3 being an internal pressure of the reaction cell.

* * * * *